United States Patent [19]

Kadowaki et al.

[11] Patent Number: 4,837,360

[45] Date of Patent: Jun. 6, 1989

[54] PROCESS FOR PRODUCING ACROLEIN AND ACRYLIC ACID

[75] Inventors: Koju Kadowaki; Kohei Sarumaru, both of Ami; Takeshi Shibano, Yokkaichi, all of Japan

[73] Assignee: Mitsubishi Petrochemical Company Ltd., Tokyo, Japan

[21] Appl. No.: 421,796

[22] Filed: Sep. 23, 1982

Related U.S. Application Data

[63] Continuation of Ser. No. 123,702, Feb. 22, 1980, abandoned.

[30] Foreign Application Priority Data

Feb. 26, 1979 [JP] Japan .................................. 54-20887

[51] Int. Cl.$^4$ .................... C07C 51/25; C07C 57/055; C07C 47/22; C07C 45/35
[52] U.S. Cl. .................................... 562/546; 502/205; 502/212; 502/241; 502/243; 502/249; 562/600; 568/479; 568/480
[58] Field of Search ................. 562/546; 568/479, 480

[56] References Cited

U.S. PATENT DOCUMENTS 3,801,634  4/1974  Krabetz et al. ...................... 562/546
3,970,702  7/1976  Shiraishi et al. ..................... 562/546

FOREIGN PATENT DOCUMENTS 1256595  12/1971  United Kingdom ................. 562/546

*Primary Examiner*—Vivian Garner
*Attorney, Agent, or Firm*—Emmanuel J. Lobato; Robert E. Burns

[57] ABSTRACT

Acrolein and acrylic acid are produced by vapor-phase catalytic oxidation of propylene in a multi-tubular, fixed-bed reaction vessel with the use of a composite oxide catalyst represented by the formula $Mo_a Bi_b Fe_c A_d B_e C_f D_g Si_h O_x$, wherein A, B, C, and D represent components selectable from respective groups of elements, and the subscripts a through h and x are specific numbers of atoms of respective elements and groups of elements. This catalyst is adapted and packed in each reaction tube in a manner such that its activity is controlled to increase from the inlet toward the outlet of the tube.

10 Claims, No Drawings

PROCESS FOR PRODUCING ACROLEIN AND ACRYLIC ACID

This is a continuation of application Ser. No. 123,702, filed Feb. 22, 1980, now abandoned.

BACKGROUND OF THE INVENTION

This invention relates generally to processes for producing acrolein and acrylic acid, particularly by vapor-phase catalytic oxidation of propylene with air or a gas containing molecular oxygen. More specifically, the invention relates to a process for producing principally acrolein and a by-product quantity of acrylic acid by catalytic oxidation of propylene at an elevated temperature with air or a gas containing molecular oxygen and with the use of a molybdenum-bismuth, multiple-component catalyst.

This oxidation reaction is accompanied by a great generation of heat and is ordinarily carried out in a multitubular, fixed-bed reaction vessel or a fluidized-bed reaction vessel. This invention relates to the use of a multitubular, fixed-bed reaction vessel.

The vapor-phase catalytic oxidation of propylene is already being industrially practiced as a reaction with the object of producing acrolein or as a first-stage reaction of a two-stage oxidation with the object of producing acrylic acid.

In the industrial practice of this oxidation reaction, a catalyst of high activity for conversion of propylene, and, moreover, a catalyst of high selectivity with respect to acrolein or with respect to acrolein and acrylic acid is required. For this reason, a great number of catalysts for this purpose have been proposed. The catalytic performances of many of these catalysts can be considered to be amply high with respect to the yield of the objective product. For example, the catalysts of Japanese Patent Publication Nos. 17711/1972, 27490/1972, 41329/1972, 42241/1972, 42813/1972, 1645/1973, 4763/1973, 4764/1973, 4765/1973, and others are said to afford the objective product or products in high yields of the order of 90 percent or higher as total yields of acrolein and acrylic acid.

However, in the case where the production of acrolein or acrolein and acrylic acid is to be practiced industrially by using these catalysts, various difficulties are encountered with respect to the realization of industrial requirements other than the yield of the objective product or products.

One difficulty arises from the industrial necessity of raising the productivity of the objective product(s). If, for this purpose, the partial pressure of the propylene in the starting material is carelessly raised, hot spots will easily form at the upstream area of catalyst, whereby there will be the danger of a runaway of the reaction. Furthermore, excessive heat generation will give rise to deterioration of the catalyst and a shortening of the catalyst life.

A simple and convenient measure for preventing the formation of hot spots is the known method of diluting parts of the catalyst of high heat generation with an inactive material. This method is disclosed in Japanese Patent Publication Nos. 9859/1959 and 24403/1968 and Japanese Patent Laid Open Nos. 10614/1972 and 127013/1976.

Another method of elevating the productivity is to increase the space velocity, whereby the reaction temperature becomes high as a natural result. However, this gives rise to a tendency toward lowering of the selectivity of the reaction and, in addition, a shortening of the catalyst life. Still another problem is that, when the temperature becomes high, there is the risk of a spontaneous oxidation reaction of the acrolein in the vapor-phase near the outlet of the reaction tube.

With the aim of solving these problems, we have carried out analytical studies relating to improvements in the characteristics of catalysts and various reactions related thereto.

As a result, we have discovered a highly effective process not seen in the prior art and have succeeded in inventing a technique which is greatly advanced for oxidizing propylene.

SUMMARY OF THE INVENTION

This invention is characterized by the composition of the catalyst used and the method of use thereof.

The catalyst is a composite catalyst represented by the formula $$Mo_aBi_bFe_cA_dB_eC_fD_gSi_hO_x,$$

wherein: A is at least one element selected from the group consisting of Co, Ni, and Mg, preferably Co or Ni; B is at least one element selected from the group consisting of P, B, and As, preferably B (boron); C is at least one element selected from the group consisting of Li, Na, and Mn, preferably Na and/or Mn; D is at least one element selected from the group consisting of K, Rb, Cs, and Tl, preferably K or Tl; a, b, c, h, and x are the relative numbers of atoms of their respective elements; and d, e, f, and g are the sum of relative numbers of atoms of their respective element groups, and, when a is 12, b is 0.4 to 7, preferably 1 to b 5, c is 0.1 to 4, preferably 0.4 to 2, d is 2 to 10, preferably 3 to 8, e is 0 to 2, preferably 0.05 to 0.5, f is 0 to 2, preferably 0.05 to 0.5, g is 0 to 2, preferably 0.05 to 0.5, and h is 0 to 60, preferably 2 to 30, and x is a relative number satisfying the valences of the elements other than the oxygen. The method of preparation and the starting materials of this catalyst in any of its forms are not limited, the preparation being possible by an ordinary suitable method.

We have studied the characteristics of the catalytic effect of each component element and each component element group of the above described composite oxide catalyst. This invention is based on the results of our study.

This invention, in another aspect thereof, is characterized by an arrangement of the catalyst in each reaction tube of the multi-tubular, fixed-bed reaction vessel wherein the catalyst is packed in the tube as a bed in a plurality of divided sections disposed successively in the tube axial direction to form the bed and respectively having activities which have been so controlled by varying the composition of the component D or/and the quantity (or quantities) of the element (or elements) thereof that the activities increase from the tube inlet toward the tube outlet.

DETAILED DESCRIPTION OF THE INVENTION

We have found that the component D in the above described catalyst of the invention, when added to a composite oxide catalyst which does not contain the component D, has the characteristic effect of improving the selectivity to the acrolein in the reaction wherein acrolein and acrylic acid are obtained by catalytic oxidation from propylene and thereby improving the total selectivity to the acrolein and the acrylic acid, but of lowering the conversion of the propylene. That is, we have found that the activity and the selectivity of the catalyst can be controlled not respectively in an independent manner, but interdependently.

Since the degree of effectiveness of the component D depends on the kind and quantity of the component D, selective adjustment of maintaining the high activity of the catalyst or imparting high selectivity thereto is made possible by varying the kind or/and quantity of the component D. Since it is impossible to attain simultaneously maximum activity and maximum selectivity, a certain balance point must be determined from the industrial viewpoint for an optimum composition, and for this purpose, the above mentioned possibility of selective adjustment is highly advantageous.

More specifically, when K, Rb, Cs, or Tl is added, the activity decreases and the selectivity increases. This effect increases with the quantity added for the same element and increase in the order Cs>Rb>K for the same quantity added. Tl has the same order to effect as Rb. Particularly in the case of the same element, the relation between the added quantity and the activity is readily determined when the production conditions are constant and therefore becomes an effective factor of high reproducibility for control of activity.

Another measure for varying the activity is changing the composition other than the component D, for example, changing the quantity of Si. This method, however, is inferior in reproducibility of activity to the method of varying the component D composition and is disadvantageous in other respects such as a great variation in properties of the resulting catalyst. However, the simultaneous use of the method depending on the component D composition and the method of varying another composition is possible and may be practiced when necessary.

Addition of the component D in a great quantity exceeding the above stated specific upper limit will cause the effect of improving the selectivity to become saturated and cause the activity to decrease greatly, whereby the value of the catalyst will be lost.

Since there is no restriction whatsoever with respect to the method of preparing the catalyst, a catalyst in a form in accordance with the purpose of use is prepared by an ordinary method. However, because of the necessity in view of the objects of this invention to produce the objective product(s) with high reaction velocity and with high selectivity, it is necessary to reduce the material diffusion resistance within the catalyst particles to a very low level by, for example, causing the particles to be as small as is allowable by the flow resistance or rendering the particles into particles of ring shape. As for the kind of catalyst, it may be a carried catalyst, an extruded catalyst, or a pelletized catalyst.

Another important feature of this invention is that the catalyst bed within each of the reaction tubes is divided into two or more sections disposed successively in the tube axis direction, and the catalytic activity is so distributed that, at the upstream part of the bed, a low-activity catalyst is disposed with emphasis placed on high selectivity, and, toward the downstream part of the bed, the activity is progressively increased while the selectivity is suppressed, this distribution being attained by changing the kind or/and quantity of the component D. The greater the number of the above mentioned sections of the catalyst bed, the more ideal will the distribution of the catalytic activity be with respect to the purpose, but it has been found that, in actual practice, excellent effects as considered industrially, which could not be realized by conventional methods, are afforded with two to four sections.

One of these excellent effects is that the arrangement of the catalyst of activity controlled in this manner makes possible not only suppression of the formation of hot spots but also the production of the objective products with high selectivity which cannot be attained by the simple dilution of catalyst bed known heretofore.

Still another important discovery we have made is that, when catalytic oxidation is carried out in a vapor phase at an elevated temperature with the use of a composite oxide catalyst containing Mo as disclosed in the present specification of the invention, one of causes which bring about deterioration of the catalyst is the sublimation of the Mo content in the composite oxide. We have found further that, even in a reaction tube of a constant-temperature system without temperature difference from the upstream and downstream parts of the catalyst bed, the degree of this sublimation is greater in the catalyst nearer the upstream part, and the deterioration of the catalyst performance is also greater toward the upstream part.

Since this sublimation tends to increase with high temperature and with the steam partial pressure of the vapor phase, the steam being conventionally used as a diluent, the heat generation of the catalyst bed results in an acceleration of the deterioration of performance. In order to suppress catalyst deterioration of this character due to sublimation of Mo, dilution of the catalyst in the upstream part of the bed in the reaction tube will suppress heat generation, whereby an effectiveness to some extent will be attained. On one hand, however, the reduction of the actual quantity of the catalyst component used which is the result of dilution gives rise to an adverse effect. Accordingly, rather than reducing the content of the catalyst component, it is more effective to use the catalyst while suppressing its activity.

By the practice of the process of this invention, a reaction in which the propylene concentration in the starting material gas is elevated is possible. As a result, the quantity of steam ordinarily used for avoiding the explosive range is reduced, whereby Mo sublimation decreases, and the catalyst life is prolonged.

The reaction may be carried out according to an ordinary once-through method or to a recycling method. The effectiveness of this invention is further pronounced under conditions of starting material composition which are industrially advantageous, such as a high propylene concentration and low steam concentration.

Except for the use of specific catalysts, which are used in a specified manner, reaction conditions for vapor-phase, catalytic oxidation of propylene to produce acrolein and acrylic acid may be those conventionally used in the art. Accordingly, the typical starting gas mixture to be subjected to the oxidation comprises 5 to 15% of propylene, 55 to 85% of air and 0 to 40% of steam, % being by volume, where the air can be partly or totally replaced by a mixture of molecular oxygen and an inert gas such as nitrogen, carbon dioxide or steam, and the steam can be partly or totally replaced by inert gas such as nitrogen, or carbon dioxide. The reaction temperature may be within the range of 270° to 350° C. The reaction pressure may be within the range of 0 to 4 kg/cm$^2$ Gage. The contact time in accordance with the equation given below may be within the range of 2 to 8 sec. The gaseous product of the reaction may be subjected to quenching and/or scrubbing with a solvent for acrolein and acrylic acid thereby to separate the acrolein and acrylic acid. In the case of two-stage oxidation for producing acrylic acid, the product gas may be mixed with air and inert gas such as steam and fed to the second-stage reactor to convert acrolein to acrylic acid. And then, the product gas is treated in such a way mentioned above to separate acrylic acid.

The catalysts to be used in the present invention may be prepared by any convenient process known or applicable for preparing conventional composite oxide catalysts. The source of the elements may be any compounds of the elements which can be decomposed upon heating into the corresponding oxide such as a nitrate, a carbonate, a carboxylate of an organic carboxylic acid such as a formate and acetate, or a polyacid of the given element or salts thereof or may be an oxide such as silica. An aqueous solution or dispersion of a mixture of the source of the required elements may be subjected to evaporation to dryness and then to decomposition under heat into the composite oxide, which may be used as the catalyst as such or in the form of tablets.

The multi-tubular, fixed-bed reaction vessel per se is also conventional in the art. This reaction vessel is alternatively called tube-and-shell reactor, and comprises a bundle of reaction tubes in which a catalyst bed is housed and a shell housing the bundle of reaction tubes. The starting mixture is passed through each of the reaction tubes, and a heating medium such as high-boiling organic liquid or nitrate mixture is passed through the shell to contact the outer surface of the reaction tubes to control the reaction temperature.

In order to indicate more fully the nature and utility of this invention, it will now be described with respect to specific examples thereof and comparison examples.

Certain terms used herein are defined below.

Contact time (sec.) =

$$\frac{\text{Apparent volume (lit.) of packed catalyst}}{\text{Volumetric flow rate (lit./h.) of starting gas mixture at reaction temperature and reaction pressure}} \times 3{,}600$$

Propylene conversion (%) =

$$\frac{\left(\begin{array}{c}\text{mols of propylene}\\\text{supplied}\end{array}\right) - \left(\begin{array}{c}\text{mols of unreacted}\\\text{propylene}\end{array}\right)}{\text{mols of propylene supplied}} \times 100$$

Acrolein yield (%) = $\frac{\text{mols of acrolein formed}}{\text{mols of propylene supplied}} \times 100$ Acrylic acid yield (%) = $\frac{\text{mols of acrylic acid formed}}{\text{mols of propylene supplied}} \times 100$ (Acrolein + acrylic acid) selectivity (%) =

$$\frac{\text{Acrolein yield + Acrylic acid yield}}{\text{propylene conversion}} \times 100$$

EXAMPLES 1, 2, AND 3

94.1 grams (g.) of ammonium paramolybdate was dissolved with heating in 400 ml. of pure water. Separately, 7.18 g. of ferric nitrate, 22.7 g. of magnesium nitrate, and 38.7 g. of nickel nitrate were dissolved at an elevated temperature in 60 ml. of pure water.

The two solutions thus obtained were gradually mixed as they were amply agitated. Then, to the resulting liquid mixture, a solution obtained by heating and dissolving 0.85 g. of borax, 0.38 g. of sodium nitrate, and 0.36 g. of potassium nitrate in 40 ml. of pure water was added, and the resulting mixture was amply agitated. Next, a solution prepared by dissolving 108 g. of bismuth nitrate in an aqueous nitric acid solution of 12 ml. of nitric acid in 98 ml. of pure water was added to the resulting mixture, and agitation was carried out. 64 g. of silica was further added to the mixture, which was further agitated and mixed.

The slurry thus obtained was heated and concentrated until it was dried and solidified. The resulting solid was heated and decomposed in an air atmosphere at 300° C. The material thus obtained was milled and formed into pellets of 5-mm. diameter and 3-mm. height. These pellets were fired in an air atmosphere at 500° C. for 4 hours and thus made into a catalyst. The composition of this catalyst calculated from the quantities of charged starting materials is a composite oxide material having the following relative numbers of atoms with respect to the metal components.

$$Mo_{12}Bi_5Ni_3Mg_2Fe_{0.4}Na_{0.2}B_{0.2}K_{0.08}Si_{24} \qquad (1)$$

In a similar manner, catalysts having the following relative numbers of metal atoms were prepared by respectively using rubidium nitrate and cesium nitrate in place of potassium nitrate.

$$Mo_{12}Bi_5Ni_3Mg_2Fe_{0.4}Na_{0.2}B_{0.2}Rb_{0.08}Si_{24} \qquad (2)$$

$$Mo_{12}Bi_5Ni_3Mg_2Fe_{0.4}Na_{0.2}B_{0.2}Cs_{0.08}Si_{24} \qquad (3)$$

The catalytic performances of these catalysts in a vapor-phase catalytic oxidation reaction under the following conditions were evaluated.

A U-shaped stainless-steel reaction tube of 17-mm. inner diameter and 300-mm. length, which was heated by a molten salt bath, was packed with a mixture of a volumetric ratio of 1:1.2 of 25 ml. of the catalyst and a diluent (mullite). The temperature of the molten salt bath was maintained at 290° C., and a gas mixture of 10 percent of propylene, 73 percent of air, and 17 percent of steam (all volumetric percentages) was caused to flow through the reaction tube under atmospheric pressure for a contact time of 4.2 sec. thereby to carry out oxidation reaction.

The results were as set forth in Table 1, which indicates that the degrees of effectiveness of K, Rb, and Cs differ.

TABLE 1

| Example No. | catalyst | propylene conversion (%) | acrolein yield (%) | acrylic acid yield (%) | (acrolein + acrylic acid) | |
|---|---|---|---|---|---|---|
| | | | | | Yield (%) | Selectivity (%) |
| 1 | (1) | 97.1 | 89.2 | 4.0 | 93.2 | 96.0 |
| 2 | (2) | 94.6 | 87.4 | 3.8 | 91.2 | 96.4 |
| 3 | (3) | 92.1 | 86.8 | 2.7 | 89.5 | 97.2 |

EXAMPLES 4, 5, AND 6

The procedure of Example 1 was followed except for the use of cobalt nitrate in place of magnesium nitrate and except for different quantities of K in catalysts (4)

and (6) thereby to prepare the following catalysts (4), (5), and (6) of the relative numbers of metal atoms as indicated.

$$Mo_{12}Bi_5Ni_3Co_2Fe_{0.4}Na_{0.2}B_{0.2}K_{0.03}Si_{24} \quad (4)$$

$$Mo_{12}Bi_5Ni_3Co_2Fe_{0.4}Na_{0.2}B_{0.2}K_{0.08}Si_{24} \quad (5)$$

$$Mo_{12}Bi_5Ni_3Co_2Fe_{0.4}Na_{0.2}B_{0.2}K_{0.3}Si_{24} \quad (6)$$

Evaluation of reactions were carried out under the same conditions as in Example 1.

The results were as shown in Table 2.

TABLE 2

| Example No. | catalyst | propylene conversion (%) | acrolein yield (%) | acrylic acid yield (%) | (acrolein + acrylic acid) yield (%) | selectivity (%) |
|---|---|---|---|---|---|---|
| 4 | (4) | 98.9 | 87.7 | 5.1 | 92.8 | 93.8 |
| 5 | (5) | 97.8 | 89.8 | 4.3 | 94.1 | 96.2 |
| 6 | (6) | 89.8 | 85.4 | 2.1 | 87.5 | 97.4 |

EXAMPLE 7 AND COMPARISON EXAMPLES 1 AND 2

Similarly as in Example 4, catalysts (of quantities of K and Si differing from those of the catalyst of Example 4) having the following relative numbers of metal atoms were prepared.

$$Mo_{12}Bi_5Ni_2Co_3Fe_{0.4}Na_{0.2}B_{0.2}K_{0.08}Si_{18} \quad (7)$$

$$Mo_{12}Bi_5Ni_2Co_3Fe_{0.4}Na_{0.2}B_{0.2}K_{0.3}Si_{18} \quad (8)$$

The above described catalysts were arranged as indicated in Table 3 in a stainless-steel reaction tube of 20-mm. inner diameter and 2,200-mm. length provided with a jacket for a heating medium and a thermocouple installed at the tube axis. Then a gas mixture of 8 percent of propylene, 67 percent of air, and 25 percent of steam was caused to flow through the reaction tube under a tube inlet pressure of 1.0 kg./cm². gage and a contact time of 3.6 sec., and reaction was carried out at bath temperatures of 310° C. and 340° C.

TABLE 3

| | Method of packing catalyst | | | |
|---|---|---|---|---|
| | Inlet preheating zone | Catalyst bed inlet part | Catalyst bed outlet part | Outlet space part |
| Comparison Example 1 | Raschig rings 100 ml | *X | Catalyst (7) 250 ml | Raschig rings 100 ml |
| Comparison Example 2 | Raschig rings 100 ml | **Y | Catalyst (8) 250 ml | Raschig rings 100 ml |
| Example 7 | Raschig rings 100 ml | Catalyst (8) 150 ml | Catalyst (7) 250 ml | Raschig rings 100 ml |

*X means a bed wherein 100 ml. of catalyst (7) and 50 ml. of porcelain Raschig rings are mixed.
**Y means a bed wherein 100 ml. of catalyst (8) and 50 ml. of porcelain Raschig rings are mixed.

The results of these reactions are shown in Table 4. In Example 7, a high total yield of acrolein and acrylic acid of 92.8 percent was obtained, indicating the high performance of the catalyst according to this invention.

TABLE 4

| | reaction bath temp. (°C.) | propylene conversion (%) | acrolein yield (%) | acrylic acid yield (%) | (acrolein + acrylic acid) yield (%) | selectivity (%) |
|---|---|---|---|---|---|---|
| Com. Example | | | | | | |
| 1 | 310 | 98.8 | 77.6 | 14.1 | 91.7 | 92.8 |
| 2-1 | 310 | 89.4 | 79.2 | 5.7 | 84.9 | 95.0 |
| 2-2 | 340 | 97.4 | 78.3 | 13.6 | 91.9 | 94.4 |
| Example 7 | 310 | 98.7 | 78.9 | 13.9 | 92.8 | 94.0 |

EXAMPLE 8 AND COMPARISON EXAMPLES 3, 4, AND 5

Similarly as in Example 4, catalysts having the following relative numbers of metal atoms were prepared, the only difference being that for the catalyst (9), manganese borate was used in place of borax, and for the catalyst (10), additionally, thallium nitrate was used in place of potassium nitrate.

$$Mo_{12}Bi_1Ni_2Co_7Fe_1Mn_{0.1}B_{0.4}K_{0.05}Si_{18} \quad (9)$$

$$Mo_{12}Bi_1Ni_2Co_7Fe_1Mn_{0.1}B_{0.4}Tl_{0.2}Si_{18} \quad (10)$$

These catalysts were packed in arrangements as set forth in Table 5, and reactions were carried out under the conditions of Example 7 except for a contact time of 4.1 sec. for the Example 8.

TABLE 5

| | Catalyst packing method | | | |
|---|---|---|---|---|
| | Inlet preheating zone | Catalyst bed inlet part | Catalyst bed outlet part | Outlet space part |
| Comparison Example 3 | Raschig rings 100 ml | *X' | Catalyst (9) 250 ml | Raschig rings 100 ml |
| Comparison Example 4 | Raschig rings 100 ml | **Y' | Catalyst (10) 250 ml | Raschig rings 100 ml |
| Comparison Example 5 | Raschig rings 100 ml | Catalyst (10) 100 ml | Catalyst (10) 250 ml | Raschig rings 100 ml |
| Example 8 | Raschig rings 100 ml | Catalyst (10) 150 ml | Catalyst (9) 250 ml | Raschig rings 100 ml |

*X' means a bed wherein 100 ml. of the catalyst (9) and 50 ml. of porcelain Raschig rings are mixed.
**Y' means a bed wherein 100 ml. of the catalyst (10) and 50 ml. of porcelain Raschig rings are mixed.

The results of the reactions are shown in Table 6. It will be observed that the total yield of acrolein+acrylic acid of Example 8 is superior to that of Comparison Example 3 and that Example 8 affords a lowering of the reaction bath temperature in comparison with Comparison Example 4. In Comparison Example 5, in which dilution of the catalyst was not carried out, a reaction with high propylene conversion was not possible because of the generation of heat.

TABLE 6

| | reaction bath temp. (°C.) | propylene conversion (%) | acrolein yield (%) | acrylic acid yield (%) | (acrolein + acrylic acid) yield (%) | selectivity (%) |
|---|---|---|---|---|---|---|
| Com. Example | | | | | | |
| 3 | 305 | 97.1 | 77.4 | 11.7 | 89.1 | 91.8 |

TABLE 6-continued

| | reaction bath temp. (°C.) | propylene conversion (%) | acrolein yield (%) | acrylic acid yield (%) | (acrolein + acrylic acid) yield (%) | selectivity (%) |
|---|---|---|---|---|---|---|
| 4 | 340 | 96.3 | 79.6 | 11.2 | 90.8 | 94.3 |
| 5 | 310 | 90.8 | 80.0 | 5.4 | 85.4 | 94.0 |
| Example 8 | 310 | 97.3 | 79.8 | 10.6 | 90.4 | 92.9 |

What we claim is:

1. The process for producing acrolein and acrylic acid by vapor-phase catalytic oxidation of propylene with molecular oxygen by using a multi-tubular, fixed-bed reaction vessel, comprising:

(a) contacting propylene with a composite oxide catalyst represented by the formula $Mo_a Bi_b Fe_c A_d B_e C_f D_g Si_h O_x$, wherein: A is at least one element selected from the group consisting of Co, Ni, and Mg; B is at least one element selected from the group consisting of P, B, and As; C is at least one element selected from the group consisting of Li, Na, and Mn; D is at least one element selected from the group consisting of K, Rb, Cs, and Tl; a, b, c, h, and x are the numbers of atoms of their respective elements; and d, e, f, and g are the total numbers of atoms of their respective element groups, b being 0.4 to 7, c being 0.1 to 4, d being 2 to 10, e being 0 to 2, f being 0 to 2, g being 0 to 2, and h being 0 to 60, and x being a number satisfying the valences of the elements other than the oxygen when a is 12; and (b) wherein in each reaction tube the catalyst is packed in the tube in a plurality of divided sections disposed successively in the tube axial direction to form the catalyst bed, said catalyst being comprised of a plurality of species of said composite oxide, respectively varying in the elemental composition of the component D, the proportion of component D as defined by g or a combination thereof, whereby the catalyst species each contain substantially the same proportion of total catalyst, but have varying activities, and wherein the catalyst species are packed respectively in said sections of the catalyst bed so that the activity of each catalyst species increases from the tube inlet toward the tube outlet.

2. The process as claimed in claim 1 in which
   (a) component A is a combination of Ni and Co or a combination of Ni and Mg, component B is P or B (boron), component C is Na or Mn and component D is K, and
   (b) the catalyst is comprised of species varying in the proportion of K, the species being packed in sections of the catalyst bed in each of the reaction tubes so that the proportion of K in each catalyst species is decreased from the tube inlet toward the tube outlet.

3. The process as claimed in claim 2 in which component A is a combination of Ni and Co, component B is boron and component C is Na.

4. The process as claimed in claim 1 in which
   (a) component A is a combination of Ni and Co, component B is boron, and component D is K or Tl, and
   (b) the catalyst is comprised of species varying in the elemental compositions of component D so arranged that component D is comprised of Tl in the section of the catalyst bed nearer the tube inlet and component D is comprised of K in the section of the catalyst bed nearer the tube outlet.

5. The process as claimed in claim 1 in which the quantity of component D in the catalyst is varied so that the activities of the thus-packed catalyst species increase from the tube inlet toward the tube outlet.

6. The process as claimed in claim 1 in which the composition of component D is varied so that the activities of the thus-packed catalyst species increase from the tube inlet toward the outlet.

7. The process as claimed in claim 1 in which b is 1 to 5, c is 0.4 to 2, d is 3 to 8, e is 0.05 to 0.5, f is 0.05 to 0.5, g is 0.05 to 0.5, h is 2 to 30 and a and x are as defined in claim 1.

8. The process claimed in claim 1 in which said propylene is contacted with said catalyst at a temperature of about 270° to 350° C.

9. The process claimed in claim 1 in which said propylene contacted with said catalyst is in a mixture containing by volume about 5 to 15% of propylene, about 55 to 85% of air and up to about 40% of steam, inert gas or a mixture thereof.

10. The process claimed in claim 1 in which the contact time of propylene with said catalyst is in the range of about 2 to 8 sec.

* * * * *